US00PP32592P2

(12) United States Plant Patent
Kopilovitch

(10) Patent No.: US PP32,592 P2
(45) Date of Patent: Dec. 8, 2020

(54) ***DIANTHUS* PLANT NAMED 'PINK FIRE'**

(50) Latin Name: *Dianthus grantianopolitanus*
Varietal Denomination: PINK FIRE

(71) Applicant: Plants Nouveau, LLC, Mobile, AL (US)

(72) Inventor: Mordehai Kopilovitch, Modi'in-Maccabim-Reut (IL)

(73) Assignee: Plants Nouveau llc, Mobile, AL (US)

( * ) Notice: Subject to any disclaimer, the term of this patent is extended or adjusted under 35 U.S.C. 154(b) by 0 days.

(21) Appl. No.: 16/602,722

(22) Filed: Nov. 26, 2019

(51) Int. Cl.
*A01H 5/02* (2018.01)
*A01H 6/30* (2018.01)

(52) U.S. Cl.
USPC ..... Plt./277

(58) Field of Classification Search
USPC ..... Plt./277, 276, 273
CPC ... A01H 5/02; A01H 5/00; A01H 6/30; A01H 6/305; A01H 5/12
See application file for complete search history.

(56) References Cited

U.S. PATENT DOCUMENTS

PP29,972 P2 * 12/2018 Hansen ..... A01H 5/02
Plt./281

OTHER PUBLICATIONS

Kovanda *Dianthus gratianopolitanus*: variability,differentiation and relationships, Preslia, Praha, 54: 223-242, 1982. (Year: 1982).*
The Perennial Farm Availability 2019, retrieved on Jun. 2, 2020, retrieved from the Internet at http://www.perennialfarm.com/images/AvailabilityRetailReady10-31-19.pdf, one page. (Year: 2019).*

* cited by examiner

*Primary Examiner* — June Hwu
(74) *Attorney, Agent, or Firm* — Cassandra Bright

(57) ABSTRACT

A new and distinct cultivar of *Dianthus* plant named 'PINK FIRE' is disclosed, characterized by fully double flowers, and intense clove fragrance. Plants rebloom in Autumn. The new variety is a *Dianthus*, typically produced as a garden or container plant.

2 Drawing Sheets

Latin name of the genus and species: *Dianthus grantianopolitanus.*

Variety denomination: 'PINK FIRE'.

BACKGROUND OF THE INVENTION

The new cultivar was found as a single chance seedling growing in a commercial planting of various *Dianthus* varieties and species. The parent varieties are unidentified.

Asexual reproduction of the new cultivar 'PINK FIRE' was first performed in Modi'in-Maccabim-Reut, Israel, in 2011 by vegetative terminal cuttings. 'PINK FIRE' has since produced several generations and has shown that the unique features of this cultivar are stable and reproduced true to type.

SUMMARY OF THE INVENTION

The cultivar 'PINK FIRE' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'PINK FIRE'. These characteristics in combination distinguish 'PINK FIRE' as a new and distinct *Dianthus* cultivar:

1. Fully double flowers.
2. More intense clove fragrance.
3. Blooms again in Autumn.

COMMERCIAL COMPARISON

Plants of the new cultivar 'PINK FIRE' are comparable to *Dianthus* 'Firewitch', unpatented, in most horticultural characteristics; however, the new variety 'PINK FIRE' differs in the following:

1. The new variety has double flowers, while this comparator has single flowers.
2. The new variety has a more intense fragrance than this comparator.
3. The new variety blooms again in Autumn, while this comparator does not.

Plants of the new cultivar 'PINK FIRE' are comparable to the commercial *Dianthus* variety 'Double Bubble', U.S. Plant Pat. No. 29,972. The two *Dianthus* varieties are similar in most horticultural characteristics; however, the new variety 'PINK FIRE' differs in the following:

1. The new variety has petals with adaxial coloration near RHS Red-Purple 70B with Red-Purple 59A striations, while this comparator has petals with mature adaxial petal color of a blend of Red-Purple 73A and 68B.
2. Foliage of the new variety has more grey tones than foliage of this comparator.
3. Petals of the new variety have dark striations in the center, while petals of this comparator do not.

Plants of the new cultivar 'PINK FIRE' are comparable to the commercial *Dianthus* variety 'Neon Star', U.S. Plant Pat. No. 14,549. The two *Dianthus* varieties are similar in most horticultural characteristics; however, the new variety 'PINK FIRE' differs in the following:

1. The new variety has double flowers, while this comparator has single flowers.
2. The new variety blooms again in Autumn, while this comparator does not.
3. The new variety is more fragrant than this comparator.
4. The new variety has larger flowers in the Spring than this comparator.

BRIEF DESCRIPTION OF THE PHOTOGRAPHS

Figure 1:
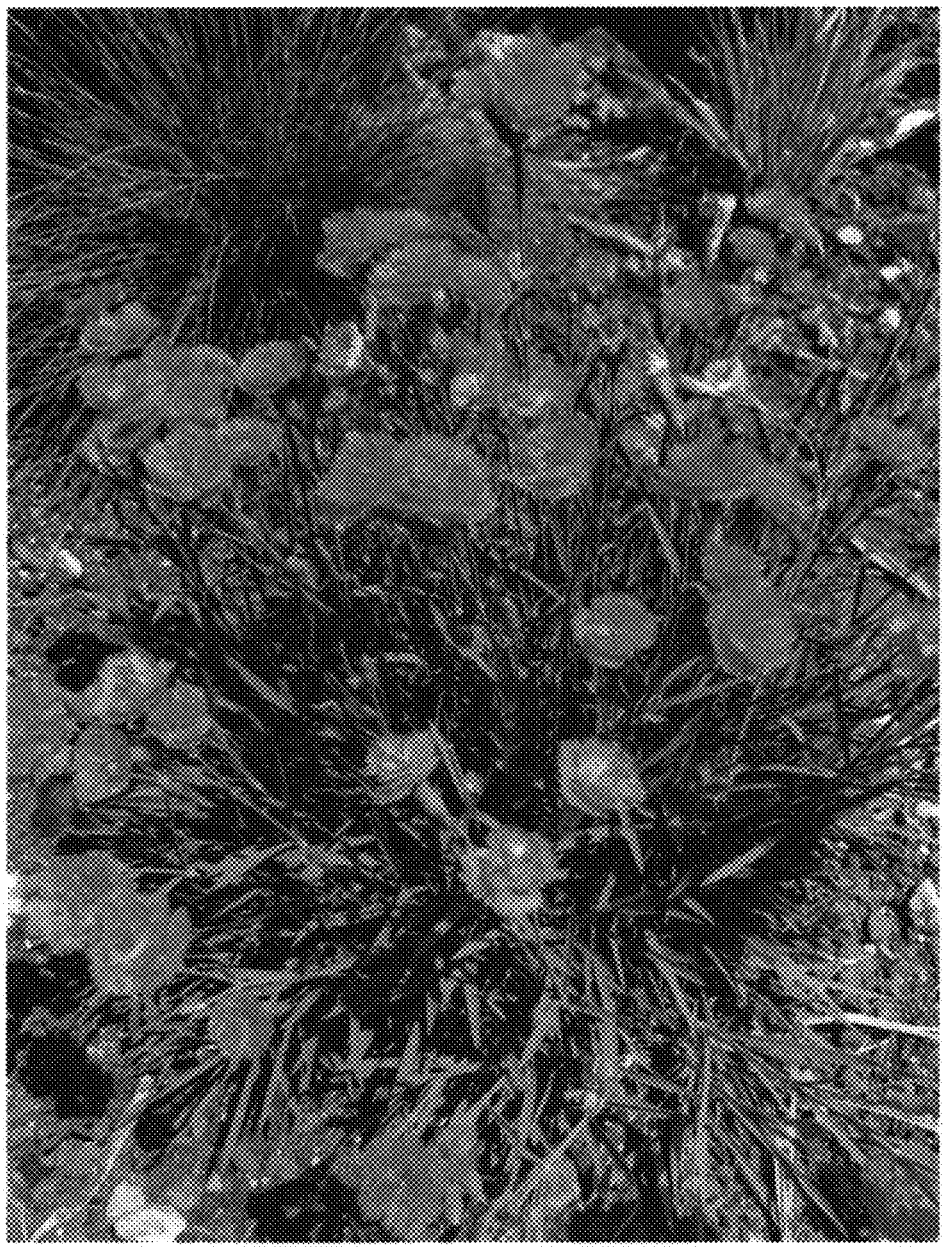

The accompanying photograph in FIG. 1 illustrates in full color a typical plant of 'PINK FIRE' grown outdoors in West Newbury, Mass. This plant is approximately 10 months old, shown in the ground.

Figure 2:
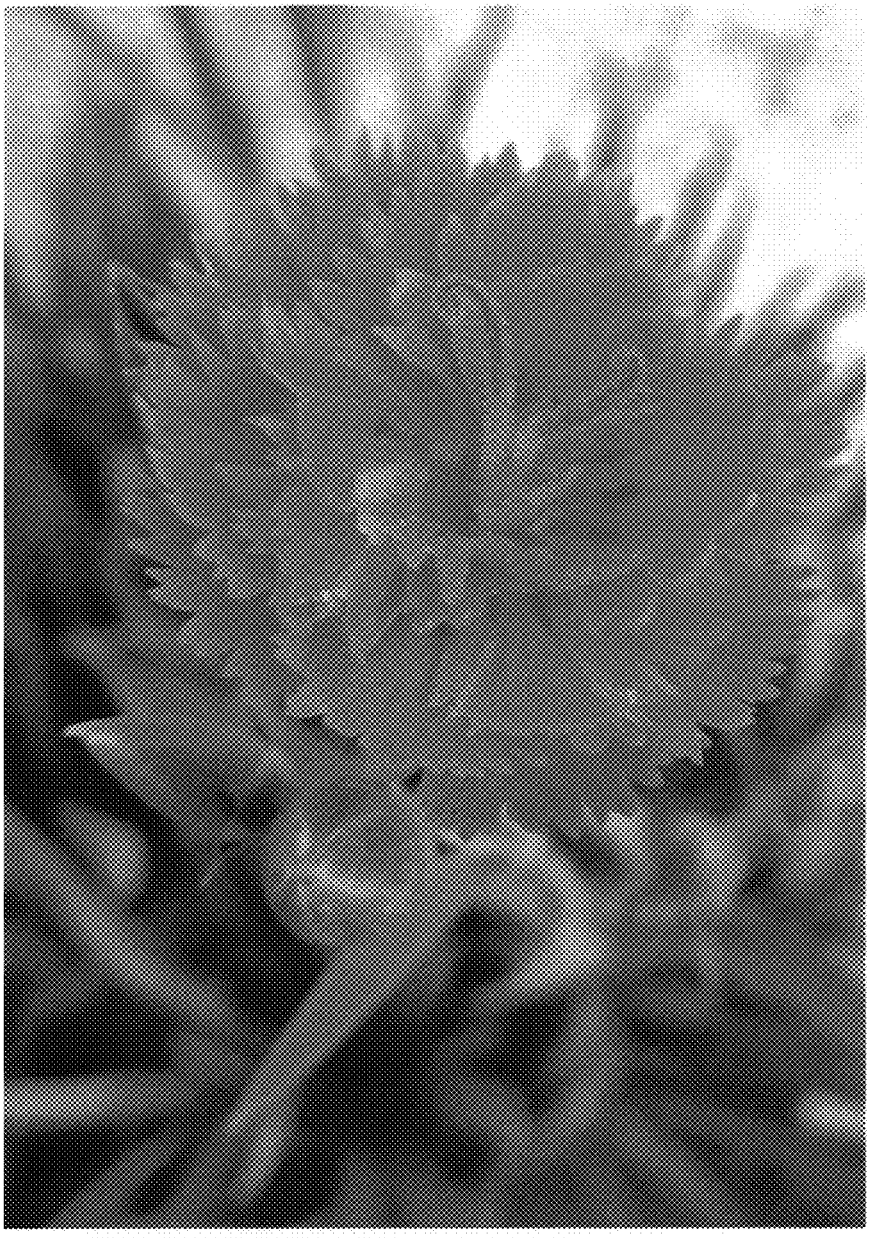

FIG. 2 illustrates a close-up view of a flower.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Colour Chart, 2007, except where general terms of ordinary dictionary significance are used. The following observations and measurements describe 'PINK FIRE' plants in a commercial greenhouse in West Newbury, Mass. Temperatures ranged from 6° C. to 35° C. night and day. No artificial light, photoperiodic treatments or chemical treatments were given to the plants. Natural light conditions were approximately 2500 to 4000 fc of light. Measurements and numerical values represent averages of typical plant types.

Botanical classification: *Dianthus grantianopolitanus* 'PINK FIRE'.

PROPAGATION

Time to initiate roots: About 10 days at approximately 24° C.

Time to produce a rooted cutting: About 18 days at 24 ° C.

PLANT

Pot size: 2 gallon.
Plant type: Compact mounding perennial.
Plant spread: Approximately 31 cm.
Height: Approximately 15 cm.
Growth rate: Quick.
Length plant stem: Average 11 cm.
Diameter of plant stem: Approximately 4-6 mm.
Quantity stems: 86.
Stem:
- *Color*.—Near RHS Greyed-Green 194A.
- *Texture*.—Woody.
- *Cross-section*.—Slightly angular, not hollow.

Internode length: Average 2 cm. 3 to 4 internodes per stem. Internodes moderately thick.

Age of plant described: Approximately 8 months from a rooted cutting.

FOLIAGE

Leaf:
- *Arrangement*.—Opposite and spiraling up the stem.
- *Quantity*.—Approximately 9 per stem.
- *Average length*.—Approximately 9 cm.
- *Average width*.—Approximately 4 mm.
- *Shape of blade*.—Linear.
- *Apex*.—Acute.
- *Base*.—Decurrent.
- *Attachment*.—Sheathing.
- *Margin*.—Entire.
- *Texture of top surface*.—Glabrous.
- *Texture of bottom surface*.—Glabrous.
- *Pubescence*.—None.
- *Attitude*.—Weakly recurved.
- *Color*.—Young foliage upper side: Near RHS Greyed-Green 191A. Young foliage under side: Near RHS Greyed-Green 191A. Mature foliage upper side: Near RHS Yellow-Green 146A. Mature foliage under side: Near RHS Yellow-Green 146A.
- *Venation*.—Type: One central vein. Venation color upper side: Near RHS Yellow-Green 144A. Venation color under side: Near RHS Yellow-Green N144D.

FLOWER

Natural flowering season: Late Spring to Summer and again in early Fall.
Flower type: Fully double.
Flower longevity on plant: 2-3 days.
Quantity of flowers: 25-30 on a 1 gallon plant.
Flowers persistent or self-cleaning: Self-cleaning.
Fragrance: Strong clove scent.
Inflorescence:
- *Flowers per*.—On average 1 to 3.
- *Total diameter*.—Average range 2 to 8 cm.
- *Height*.—Approximately 4 to 5 cm.
- *Position above foliage*.—Moderately above foliage.

Individual flower size:
- *Diameter*.—Approximately 2 cm.
- *Length*.—Approximately 3 cm.

Petals:
- *Shape*.—Linear base, deltoid uppermost section.
- *Petal arrangement*.—Fully double, whorled.
- *Margin*.—Dentate. Many deep incisions.
- *Apex*.—Dentate lobes.
- *Length*.—1 cm.
- *Width*.—1 cm.
- *Petal quantity*.—Average 18.
- *Texture*.—Glabrous all surfaces.
- *Aspect*.—Mostly flat.

Color:
- *When opening*.—Upper surface: Near RHS Red-Purple 72A. Lower surface: Near RHS Red-Purple 70B.
- *Fully opened*.—Upper surface: Near RHS Red-Purple 70B with few to moderate Red-Purple 59A striations. Lower surface: Near RHS Red-Purple N74A at the tip, fading to Purple 76B at the base.
- *Fading*.—Upper surface: Near RHS Red-Purple 70B with moderate Red-Purple 59A striations. Lower surface: Near RHS Red-Purple N74A at the tip, fading to Purple 76B at the base.

Petal linear base:
General description: Tube consists of the elongated, unfused base of the petals. Tube shape caused by a fused calyx.
- *Length*.—2 cm.
- *Width*.—3 mm.
- *Texture*.—Smooth.

Color:

*When opening*.—Upper surface: Near RHS Yellow-Green 149D. Lower surface: Near RHS Yellow-Green 149D.

*Fully opened*.—Upper surface: Near RHS Yellow-Green 149D. Lower surface: Near RHS Yellow-Green 149D.

*Fading*.—Upper surface: Near RHS Yellow-Green 149D. Lower surface: Near RHS Yellow-Green 149D.

Bud:

*Shape*.—Cylindrical.

*Length*.—Average 1.5 cm.

*Diameter*.—Average 7 mm.

*Color*.—Near RHS Yellow-Green 144A. Emerging flower color near RHS Red-Purple 72A.

Calyx:

*Shape*.—Cylindrical.

*Length*.—Approximately 1.5 cm.

*Width*.—Approximately 3 mm.

*Margin*.—Entire.

*Apex*.—Acute.

*Texture*.—Smooth.

*Color*.—Near RHS Yellow-Green 144A.

Bracteoles:

*Shape*.—Linear.

*Quantity per flower*.—2.

*Length*.—Approximately 2.5 cm.

*Width*.—Approximately 2 mm.

*Margin*.—Entire.

*Texture*.—Glabrous.

*Color*.—Near RHS Green 137A.

Peduncle:

*Length*.—Average 1 cm.

*Diameter*.—1 mm.

*Color*.—Near RHS Green 138B.

*Orientation*.—Upright.

*Strength*.—Strong.

Pedicel:

*Length*.—Average 4.5 cm.

*Diameter*.—1 mm.

*Color*.—Near RHS Green 138A.

*Orientation*.—Upright.

*Strength*.—Strong.

REPRODUCTIVE ORGANS

Stamens:

*Number*.—7.

*Filament length*.—Approximately 1 cm.

Anthers:

*Shape*.—Rounded, oblong.

*Length*.—Approximately 2 mm.

*Color*.—Near RHS Yellow-Green 150D.

*Pollen*.—Not observed to date.

Pistil:

*Number*.—2.

*Length*.—Approximately 2 cm.

*Style*.—Length: Approximately 1.5 cm. Color: Near RHS White N155D.

*Stigma*.—Shape: Linear with a twist at the end. Color: Near RHS Purple N78C. Ovary color: Near RHS Yellow-Green 145B. Ovary shape: Obovate. Ovary diameter: 3 mm. Ovary length: 1.2 cm. Ovary surface texture: Slightly ribbed.

OTHER CHARACTERISTICS

Seeds and fruits: Very tiny, round, black seed. Approximately 20.

Disease/pest resistance: Neither resistance nor susceptibility to the normal diseases and pests of *Dianthus* has been observed. Typical diseases of *Dianthus* include: *Alternaria dianthicola, Botrytis cinerea, Erwinia chrysanthemi, Pseudomonas caryophylli, Fusarium graminearum, Fusarium avenaceum, Fusarium culmorum* and *Rhizoctonia solani*, Typical pests include; various species of *Thysanopthera*, various *Aphis* species, and various species of *Tetranychus*.

Temperature tolerance: USDA zones 5 through 10 tolerant.

What is claimed is:

1. A new and distinct cultivar of *Dianthus* plant named 'PINK FIRE' as herein illustrated and described.

* * * * *